(12) United States Patent
Hubbuch et al.

(10) Patent No.: US 8,474,336 B2
(45) Date of Patent: Jul. 2, 2013

(54) METHOD FOR DEPOSITING SAMPLES IN MODULES AND AN ADAPTER

(75) Inventors: Juergen Hubbuch, Karlsruhe (DE); Tim Schroeder, Dueren (DE); Pierre Beugre, Duesseldorf (DE); Matthias Wiendahl, Hillerod (DK)

(73) Assignee: Atoll GmbH, Weingarten (DE)

( * ) Notice: Subject to any disclaimer, the term of this patent is extended or adjusted under 35 U.S.C. 154(b) by 384 days.

(21) Appl. No.: 11/919,776

(22) PCT Filed: Apr. 25, 2006

(86) PCT No.: PCT/DE2006/000708
§ 371 (c)(1),
(2), (4) Date: May 19, 2010

(87) PCT Pub. No.: WO2006/116964
PCT Pub. Date: Nov. 9, 2006

(65) Prior Publication Data
US 2010/0242634 A1    Sep. 30, 2010

(30) Foreign Application Priority Data

| May 3, 2005 | (DE) | 10 2005 020 983 |
| Jun. 8, 2005 | (DE) | 10 2005 026 585 |

(51) Int. Cl.
*B01L 3/02* (2006.01)

(52) U.S. Cl.
USPC .................................................. 73/864.21

(58) Field of Classification Search
None
See application file for complete search history.

(56) References Cited

U.S. PATENT DOCUMENTS

| 3,327,520 | A | * | 6/1967 | Stapp, Jr. ..................... 73/23.41 |
| 3,581,573 | A | * | 6/1971 | Purcell et al. ............. 73/863.11 |
| 3,682,315 | A | | 8/1972 | Haller |
| 3,884,802 | A | * | 5/1975 | Spaans et al. ................. 210/656 |
| 4,414,857 | A | * | 11/1983 | Brazhnikov et al. ........ 73/863.11 |
| 4,563,275 | A | | 1/1986 | McEachern |
| 4,615,226 | A | * | 10/1986 | DiNuzzo et al. ............ 73/864.87 |
| 4,619,473 | A | | 10/1986 | Someya |
| 4,732,046 | A | * | 3/1988 | Lawrence et al. .......... 73/864.21 |
| 4,854,181 | A | * | 8/1989 | Gerstel ...................... 73/863.86 |
| 4,888,998 | A | * | 12/1989 | Buzza et al. ............... 73/864.21 |
| 5,324,427 | A | * | 6/1994 | Traveset-Masanes et al. ........... 210/198.2 |
| 5,738,783 | A | * | 4/1998 | Shirota et al. ............. 210/198.2 |

(Continued)

FOREIGN PATENT DOCUMENTS

| DE | 2026329 A | 12/1971 |
| DE | 2447508 A1 | 4/1975 |

(Continued)

OTHER PUBLICATIONS

Office Action in the basic German procedure, DE 10 2005 026 585.5, dated Mar. 7, 2007.
Search Report for EP 10009331, EPO, Rijswijk, NL, issued Oct. 31, 2011.
Search Report for EP 10009335, EPO, Rijswijk, NL, issued Oct. 28, 2011.

*Primary Examiner* — Robert R Raevis
(74) *Attorney, Agent, or Firm* — Harness, Dickey & Pierce, P.L.C.

(57) ABSTRACT

The invention relates to a method for depositing samples in modules, in particular, in kits, in addition to an adapter. The inventive adapter (1) is embodied in such a manner that an injection needle can be received in a liquid-tight manner. It is connected in a liquid-tight manner to the low-lying module or kit (20) and enables a continuous flow of samples.

35 Claims, 5 Drawing Sheets

U.S. PATENT DOCUMENTS

Figure 1:
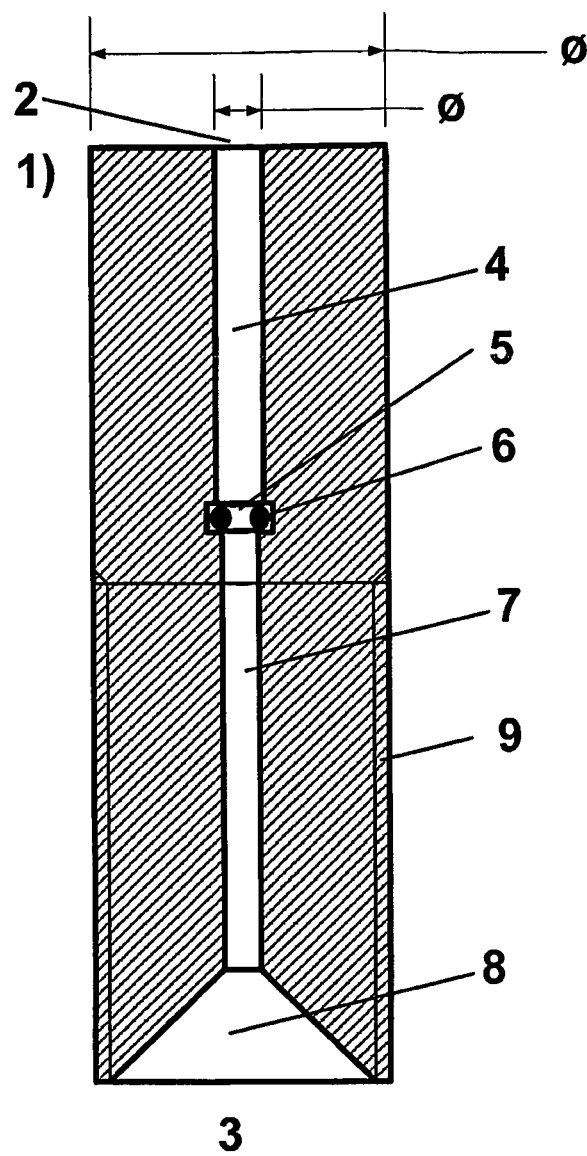

| | | |
|---|---|---|
| 6,193,286 B1 | 2/2001 | Jones et al. |
| 6,494,500 B1 | 12/2002 | Todosiev et al. |
| 7,669,489 B2 * | 3/2010 | Staples et al. ............. 73/864.24 |
| 7,709,267 B2 * | 5/2010 | Tipler et al. ................. 436/178 |
| 2002/0142336 A1 | 10/2002 | Smith et al. ...................... 435/6 |
| 2004/0028179 A1 | 2/2004 | Rosso et al. ..................... 378/70 |

FOREIGN PATENT DOCUMENTS

| | | |
|---|---|---|
| DE | 19712195 | 9/1998 |
| WO | WO 01/21310 A2 | 3/2001 |
| WO | 02/088672 A1 | 11/2002 |
| WO | 03/036304 A1 | 5/2003 |

* cited by examiner

METHOD FOR DEPOSITING SAMPLES IN MODULES AND AN ADAPTER

CROSS REFERENCE TO RELATED APPLICATIONS

This application is the US national phase of PCT application PCT/DE2006/000708, filed 25 Apr. 2006, published 9 Nov. 2006 as WO 2006/116964, and claiming the priority of German patent application 102005020983.1 itself filed 3 May 2005 and German patent application 102005026585.5 itself filed 8 Jun. 2005, whose entire disclosures are herewith incorporated by reference.

The invention relates to a method and adapter for adding samples to modules.

A module is here also be construed to be a kit, depending on the application.

In laboratory operations, in particular in high throughput screening (HTS) methods according to the state of the art, liquid samples are supplied by means of pipetting stations to modules, in particular kits, in which the liquid samples are for instance filtered, absorbed, or eluted. A module is here understood to be an open container with an inlet and outlet for liquids having, but not limited to, for instance a column-like shape that is filled with a stationary porous solid mass. A module is in particular construed to be a kit. The bottom of this vessel is liquid permeable. The solid mass can be embodied differently and can be, but is not limited to, for instance a filter, a membrane, or a liquid-distributing or chromatography substrate. The liquid added flows through the porous solid mass and leaves the module via an outlet in the bottom of the module. As a rule the exiting liquid is collected in a collecting vessel. Depending on the application, a module is construed to be a kit for, but not limited to, for instance purifying macromolecules (proteins or nucleic acids), filtering suspensions, cultivating cells, or medical technology. Applications are found for instance in preparing products from biotechnological processes, purifying proteins, or in medical technology, e.g. analyzing blood specimens.

The driving force that causes the liquid to flow through the porous solid mass is applied either using a centrifuge or with a vacuum or positive pressure. The positive pressure is applied above at the input to the module, the vacuum is applied below at the output of the module.

The samples are typically added to the modules in batch operations. The sample volume that can be added to the module is limited by the volume of the modules. If a sample volume that is larger than the volume of the module is to be added, the sample must be added in batches. Some of the sample volume is added, and the sample volume is allowed to flow through the module by applying a driving force. This process is repeated until the entire sample volume has been treated. As a rule, the standard module used is a cylindrical or conical vessel with liners. The latter can be bottom liners such as filters or membranes, but they can also be chromatography materials. All of the liners are available commercially. The invention is in particular intended for commercial modules, but is not limited to the use thereof.

The term "pipetting needle" is used in the following; however, it also encompasses other essentially needle-shaped designs, such as for instance pipette tips through which the samples can be metered. According to the prior art, the samples are supplied to the modules by means of pipetting needles in batch operations.

This manner of operating results in the following disadvantages, however:

It is very time-consuming to perform this method. It is only possible to work with small volumes, and the quality in particular of chromatography treatment and of the eluate obtained does not reach the desired level. Another disadvantage is only indirect control of the speed with which the liquid flows through the module and of the pressure on the liquid that has been added. It is not possible to add larger sample quantities continuously due to the limitation of the module or kit volume.

It is therefore the object of the invention to create a method and an apparatus with which, in a specified period of time, a larger sample quantity can be applied, preferably in a single step, or a number of a plurality of samples can be applied in series. The quality of the tests performed, the time saved, and the handling and quality of the samples obtained should be improved.

Proceeding from the preamble to claim 1, the object is inventively attained with the features provided in the characterizing portion of claim 1.

In particular it is now possible to apply larger quantities of samples in a shorter period of time with improved product quality when using kits/modules.

Advantageous further embodiments of the invention are provided in the subordinate claims.

The figures show preferred embodiments of an inventive adapter.

Figure 2:
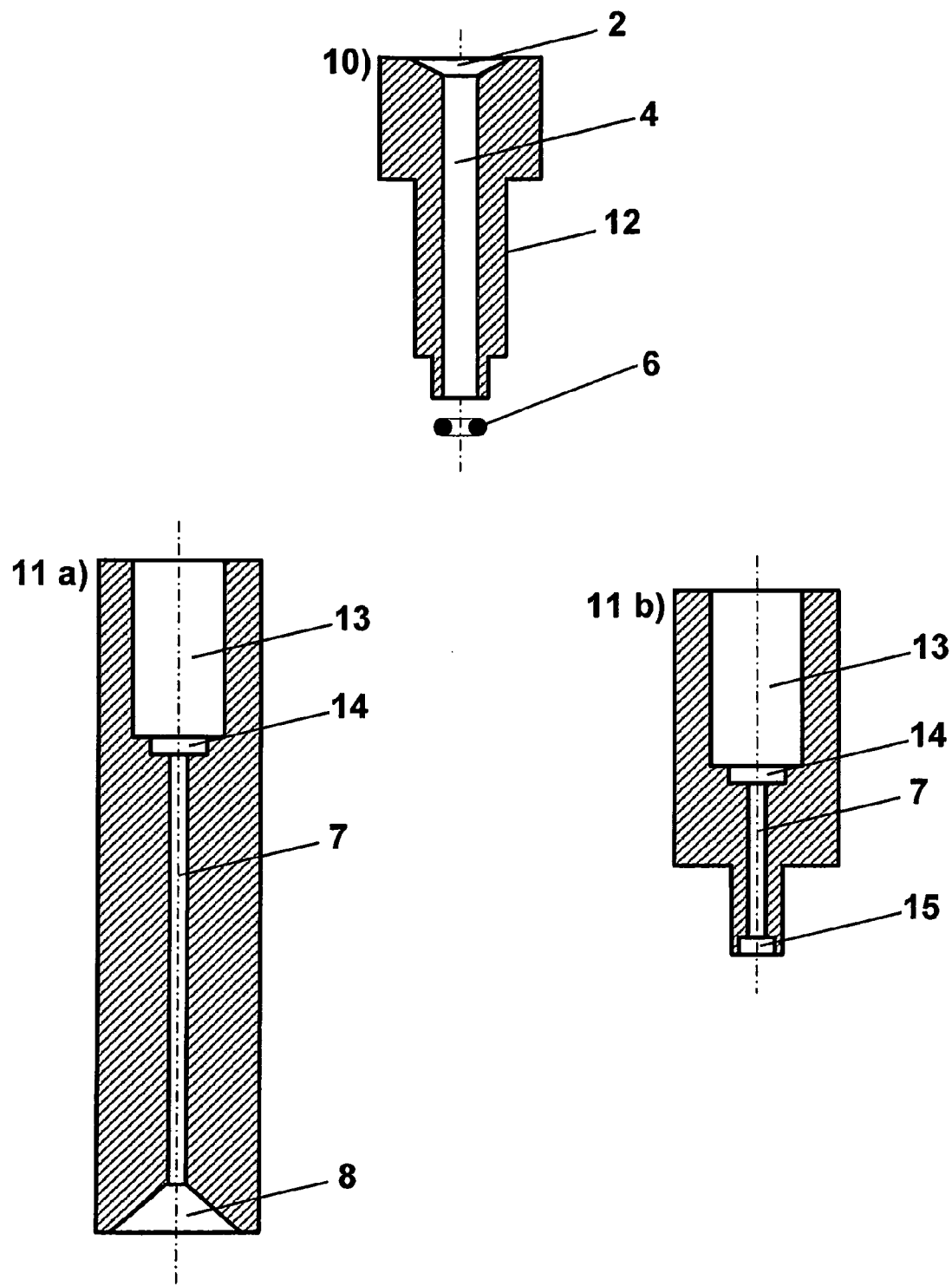
Figure 4:
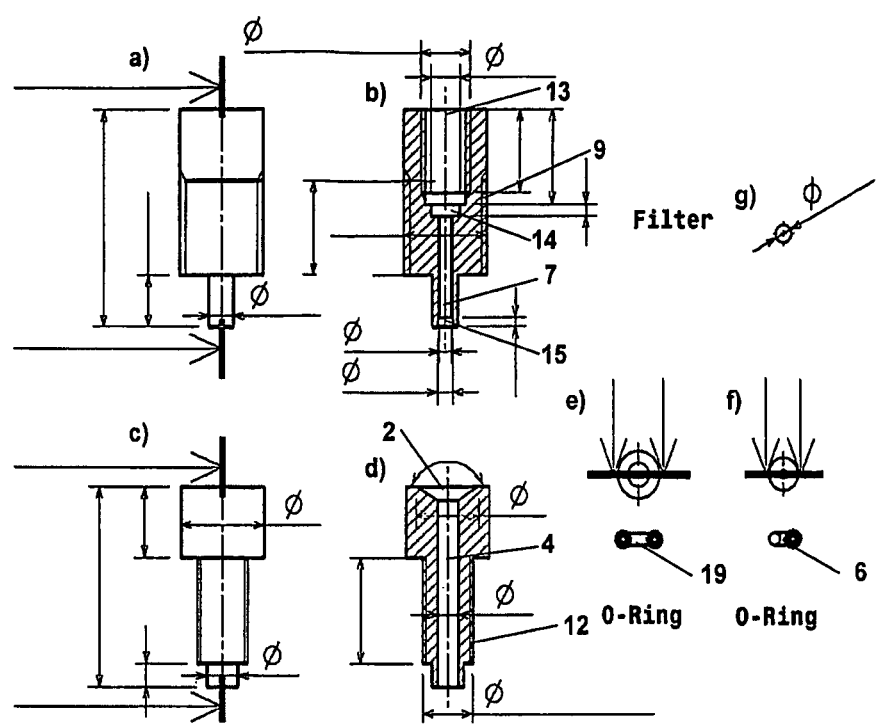
Figure 5:
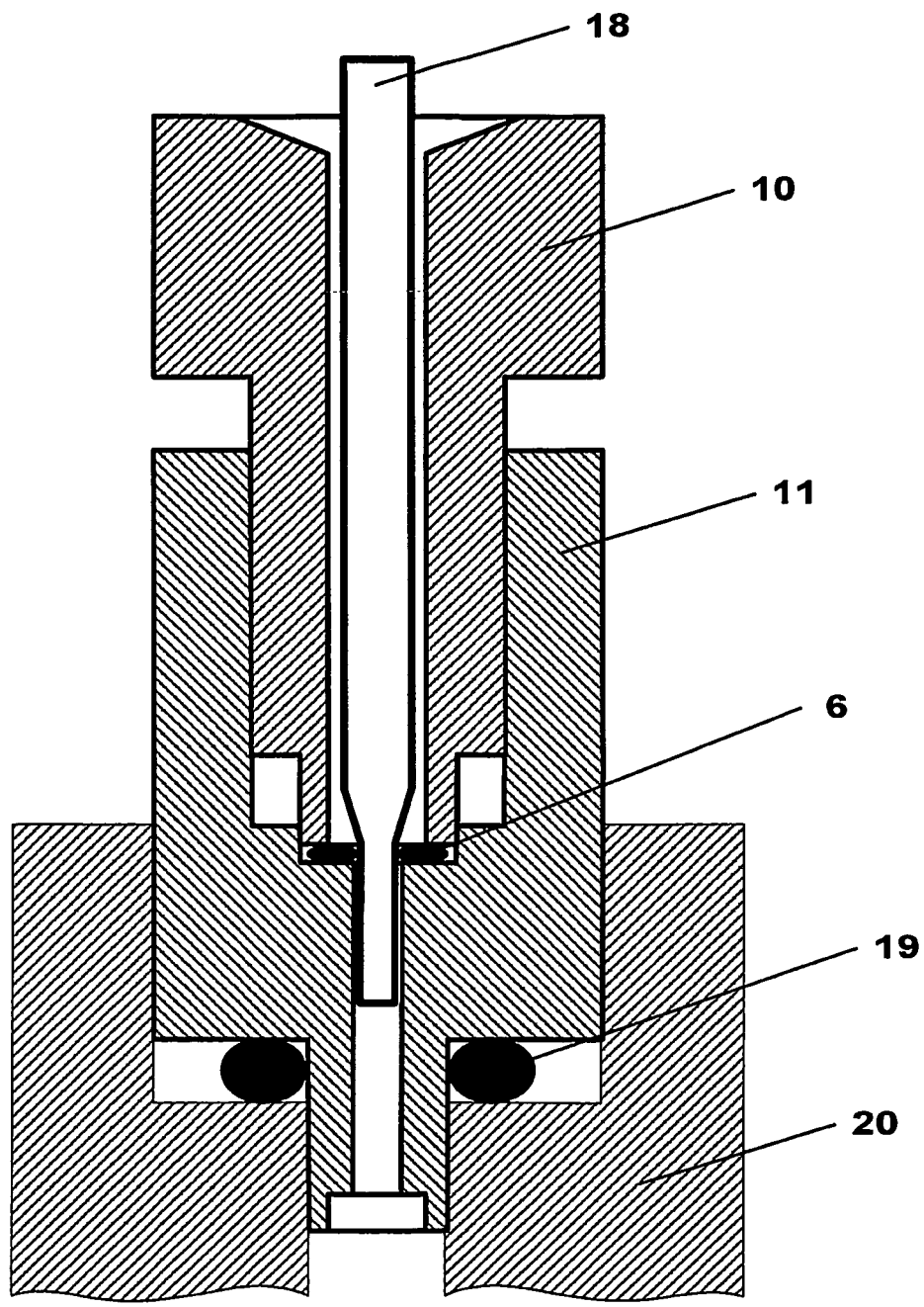

FIG. 1 is a one-piece adapter;
FIG. 2 is a two-piece adapter;
FIGS. 3a and 3b show an adapter having a two-channel inlet;
FIG. 4 is a detailed depiction of the adapter;
FIG. 5 is an illustrated embodiment of the inventive adapter.

FIG. 1 shows a one-piece embodiment of the inventive adapter 1. It has an input 2 and an output 3. The input 2 opens into an upper bore 4 that is extended as a lower bore 7 that widens in the shape of a funnel 8. A pipetting needle can be received in the bore 4. A screwthread 9 is optionally provided in the lower portion of the adapter 1. A groove 5 between the upper and the lower bores 4 and 7 holds an O-ring 6 that can fit around a pipetting needle and is an example of a seal means.

FIG. 2 shows a two-piece embodiment of the inventive adapter 1 having different lower parts 11a and 11b and an upper part 10 that can be inserted into each of these lower parts 11a and 11b. The upper part 10 has a funnel-shaped input 2 for receiving a pipetting needle. It has a portion 12 that can be inserted snugly into a portion 13 of the lower part that receives the upper part 10. The portion 13 of the lower part 11a or 11b that receives the upper part 10 has a constriction 14 that can receive an O-ring. The portion 13 of the lower part 11a or 11b that receives the upper part 10 narrows at the lower bore 7 that can receive the pipetting needle and through which furthermore the exiting liquid flows. The lower bore 13 [sic] widens at the output in the shape of a funnel 8 or in the shape of a cylindrical widened region 15.

Figure 3:
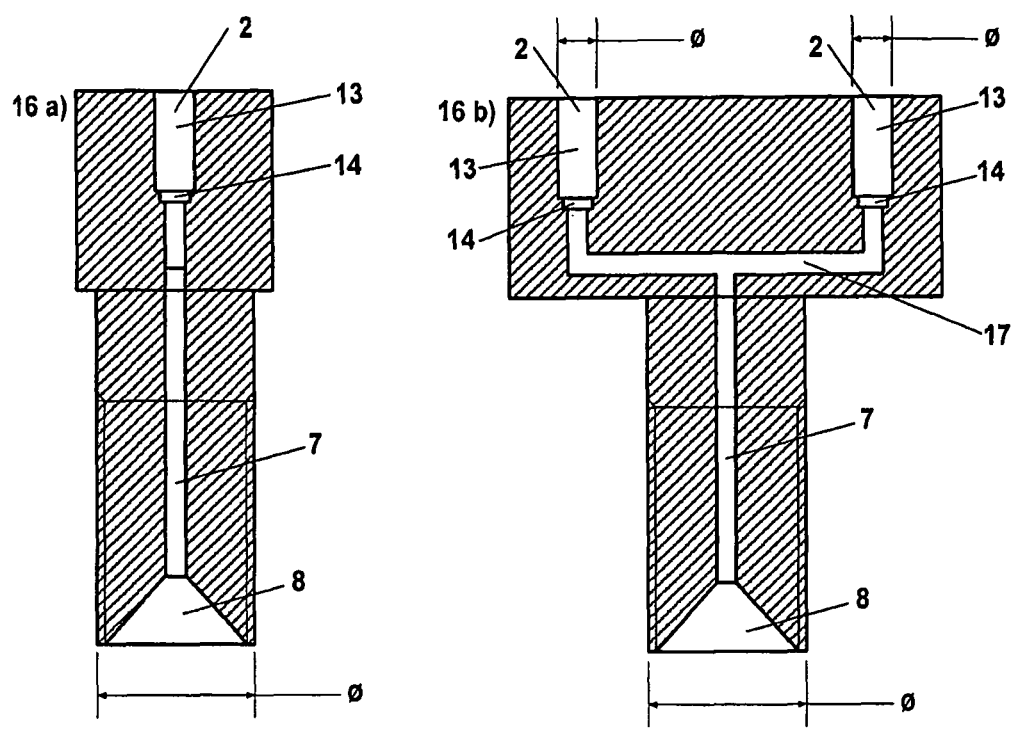

FIG. 3 shows one embodiment of the inventive adapter 1 that has two input ports 2 for liquid. The part 16a is shown in side elevation and the part 16b is shown in front elevation. In FIGS. 3a and 3b the same features receive the same reference numerals. Two portions 13 that receive pipetting needles are connected to the lower bore 7 via a manifold passage 17.

FIG. 4 shows a specific illustrated embodiment for an inventive adapter 1 in views a, b, c, and d, views a and b being the lower part and views c and d being the upper part of the two-piece embodiment, and also shows the O-rings that fit these parts in views e and f and shows a filter in view g. FIG. 4b shows a section through FIG. 4a and FIG. 4d shows a section through FIG. 4c. In this case as well, equivalent apparatus features have the same reference numbers.

FIG. 5 shows an inventive adapter having a pipetting needle 18 that is inserted into the upper part 10 of a two-piece adapter and the tip of which projects into the lower part 11 of the two-piece adapter 1. An O-ring 6 is provided in the intermediate space between the upper and lower parts 10 and 11 of the adapter. The adapter 1 is placed on a module/kit 20 and is sealed with another O-ring relative to the input of the module/kit 20.

When using the inventive adapter, a liquid sample is generally added to the module/kit 20 using a pipetting needle or a pipette tip via an adapter 1.

A module 20 in the context of the invention is here construed as but not limited to an open container having an inlet and outlet for liquid, for instance, in a column shape, that is filled with a stationary porous solid mass. The bottom of this vessel is liquid-permeable. The solid mass can be designed in different ways and can be, but is not limited to, for instance a filter, a membrane, or a liquid-distributing or chromatography substrate.

Depending on the purpose of the module, it shall include in particular a kit. A kit is here construed as but not limited to an analysis kit, for instance a diagnostic kit, an RNA isolating kit or a PCR kit, or a kit for separating or purifying proteins. Such kits can be used in the field of microbiology, biotechnology, and medical technology. In one preferred embodiment, the inventive module therefore largely has the standard dimensions for kits. Typical target applications for kits are rapid separation, good separating performance, and high recovery of valuable samples. The typical formats for kits are individual kits, 8-strip kits, and 96 microtiter plate (8×12) kits. The kits function for instance selective binding (adsorption) of certain proteins to a primarily solid mass (also called adsorbers), e.g. a membrane or chromatography adsorber particles. The adsorber can selectively adsorb certain proteins; all other samples flow through the kit without binding. In a second step the bonded proteins are released, eluted or desorbed, and are then present in a greater purity. Alternatively, the product can represent the molecules that flow through, while undesired constituents bind to the solid mass.

The term "pipetting needle" is used in the following. However, it also encompasses other essentially needle-shaped structures through which the samples can be metered, such as for instance pipette tips.

The adapter 1 produces a liquid-tight connection between the pipetting needle and the module 20 via which sample can be added.

The adapter 1 is embodied in a single part in one embodiment and includes an input 2 and an output 3.

The output 3 is connected to the module 20 in a liquid-tight manner. For this purpose, the output 3 or the lower part of the adapter 1 can be embodied to be fitted liquid-tight to the module 20. Moreover, at least a lower portion of the adapter 1 can have a screwthread 9 that can be screwed into the input of a module 20. The screwthread 9 is for instance for fitted sealing connections.

For connecting to the module 20 in a liquid-tight manner, the output 3 of the adapter 1 is preferably equipped with seal means. This can be for instance be an O-ring, adhesive film, film, or a diaphragm. Also conceivable is a male screwthread that is enclosed where necessary with a sealing mass.

Depending on the design of the module, the adapter 1 can be a securely seated integral component of the module or kit so that it is permanently connected. This applies both for the one-piece and for the two-piece embodiment.

In a preferred embodiment, the outlet 3 preferably has a sample outlet that has a shape enabling the liquid to exit uniformly across the entire cross-section of the sample exit. This liquid outlet is preferably uniform across the entire inlet surface of the module/kit 20. This can be effected for instance in that the sample outlet is shaped as a largely conically outgoing hollow space, for instance in the shape of a funnel 8 or a step-like hollow space 15 that tapers inward largely in a radially symmetrical manner from the outlet end. Alternative options for uniform liquid distribution across the entire cross section of the outlet can be liners such as for instance membranes, perforated plates, or filter disks. The latter are examples of means for uniformly distributing liquid across the cross-section of the output.

In one preferred embodiment, the adapter 1 is embodied such that the sample outlet or the output 3 with the bottom part of the module 20, for instance the filter, membrane, or chromatography substrate, does not permit any dead volume or permits a small dead volume. This means that the sample outlet or the output 3 is largely sealed with the bottom of the module or that only a small liquid volume, preferably without any gas, is above the bottom of the module. This guarantees a particularly good quality test or method.

The outside diameter of the outlet 3 is largely the same as the inside diameter of the module 20 and is therefore preferably set to the dimensions of commercially available and standardized inside diameters of kits. They are for instance 4 mm, 6 mm, or 6.5 mm. However, the outside diameters can also be freely selectable to match the inside diameters of for instance non-standard vessels and vessels produced in-house. Overall it depends on the function of the liquid-tight contact between the adapter 1 and the module 20.

In one embodiment the inlet 2 of the adapter 1 is embodied such that it permits the sample to be received in a liquid-tight manner.

For this purpose the inside diameter of the input area of the adapter 1 is largely the same as the outside diameter of the pipetting needle so that ideally tight fit is created. Alternatively or in addition thereto the adapter 1 can be sealed liquid-tight at its input 2 with a septum.

The bore 4 can have a larger inside diameter than the bore 7.

In one preferred embodiment, an O-ring that surrounds the pipetting needle is received for instance in a constriction 14. The inside diameter of the O-ring is preferably smaller than the outside diameter of the pipetting needle so that the O-ring encloses and seals the pipetting needle so that liquid can flow only in the direction of flow.

Moreover, the input 2 of the adapter 1 can be provided with seal means that make it possible to add the sample to the adapter 1 in a liquid-tight manner. These seal means can also be O-rings or diaphragms or adhesive films.

In one embodiment, the input 2 can be fitted with a liquid-tight connection that makes it possible to attach a tube-like sample feed line. This sample feed line can be a flexible, preferably pressure-resistant, line that enables for instance connection to a pump system for supplying liquid or to other process steps upstream of the module/kit 20.

Such lines can be fastened for instance using compression fittings with union nuts and where necessary additional seal means. Preferably the adapter is sealed against the module 20 and the pipetting needle is sealed against the adapter.

The adapter 1 connected to the module 20 preferably permits an internal pressure load of 0.2 MPa, better up to 0.3 or 0.5 MPa, very particularly preferred 1 MPa.

In another embodiment the adapter 1 is made of two parts and includes a lower part that faces the module 20 and an upper, separated inlet part. In this case it is possible to combine different input and output parts with one another so that the adapter 1 can be used in a variety of ways.

The upper and lower parts 10 and 11 of the two-piece adapter 1 can be connected to one another for instance using a screw connection or a plug-in connection. This connection is itself preferably liquid-tight and preferably includes seal means. It is preferably likewise pressure-resistant, like the one-piece unit.

In another embodiment of the invention, the input 2 of the adapter 1 can be made such that it can receive at least two pipetting needles or feed lines. In general an adapter 1 can have n inputs that open into a manifold passage 17 so that it is possible to mix different components. n can be 10-2, preferably 5-2, particularly preferred 2. This makes it possible to mix different sample liquids with one another. The feed lines for these liquids can follow certain metering rules so that defined compositions can be attained.

In a further development of the invention, at least two adapters 1 can be provided together so that a plurality of modules 20 that are arranged in rows or in a preferably rectangular grid can be operated simultaneously.

This arrangement can contain 2, 4, 8, 96, or more adapters 1 in a row or in another orientation, for instance a circle or section of a circle or another rounded shape. In this case an adapter is here construed to be an adapter and also the arrangement by means of a manifold passage 17. An arrangement is preferably in rows or rectangular structures.

The inventive adapter enables continuous operation in that the sample is added to the kit or module 20 in a continuous process, preferably under pressure. Because of this, there is no need for batch operation in which the module 20 is evacuated either by repeated suctioning or with pressurization that is applied after the pipette has been removed. There is also no need for centrifuging. All of these methods are time-intensive, material-intensive, and machine-intensive steps that can be eliminated. The samples that have been added do not have to be split up.

The invention also includes a method for filling modules 20 in which method the samples metered into the modules 20 are inventively added to the modules in continuous-flow operations. The method is in particular characterized in that the samples can be added to the module 20 continuously and liquid-tight through a pipetting needle. For this purpose the sample is supplied to the module 20 in continuous operation. The sample is supplied, by means of a pump through a pipetting needle via a liquid-tight connection to the module 20 and flows therethrough. The bottom of the module 20 can be a filter, membrane, or adsorber. The sample then leaves the module 20 and can be sent on to additional method steps. The sample is preferably conducted via an inventive adapter.

Moreover, different samples can be supplied to a module 20 in parallel and mixed with one another.

Moreover with the inventive method different modules can be positioned simultaneously in parallel and in series so that productivity can be increased.

One particular advantage is the improvement in quality for the test or method. This quality improvement is effected e.g. by the interruption-free passage of the sample through the medium, for instance the filter, the chromatography solid, or the membrane, since an uninterrupted flow of liquid leads to the best separation or elution results. In particular in the case of chromatography interruption-free operation is an important measure for quality assurance. Precise flow-through parameters can be set, for instance in that a feed pump delivers according to requirements. For loading kits or modules 20, mixed metering of the sample is possible for the first time, which makes it possible to set elution conditions in gradients or steps. Moreover samples or substances that react with one another can be mixed.

Samples can be added to kits or modules 20 with the inventive adapter 1. The applications are in particular characterization and development of modules/kits 20, testing the methods that are represented by the modules/kits 20, or use of these modules/kits 20 for treatment or purification of samples.

In this invention an adapter was designed that permits small columns or column-like containers to work with pipette tips directly, with commercially available formats that are used on HTS platforms, and permits them to be operated in flow-through mode. The adapter can be used as an individual part, strips (linear combination of adapters), or in a multi-well format. On the lower side the adapter offers the option of connecting it to all common formats for multi-well plates, columns, membrane stacks, or containers, while at the upper end it can use pipette tips using a sealing device. Liquid distribution at the lower end is ensured, depending on the application, using common techniques such as e.g. conical outlet, membrane/filter closure, distribution plate.

This offers the following advantages:

Flow-through applications are possible.

Extreme time savings for screening and HTS applications.

Quantity added is limited only by pump capacity and is a multiple of prior-art quantities added.

It is possible to set flow rates precisely.

Very precise and rapid sample fractionating becomes possible.

Elution processes attain better results.

It is possible to compare directly to scalable techniques that are operated in flow-through operations.

For validating and recording additional measured values, it is desirable to connect the application to common chromatography systems, as well. Therefore the upper adapter part offers the opportunity to connect common connectors for chromatography systems and to operate the application in question with them.

In order to be able to apply liquid mixtures that change over time (elution studies), there is furthermore the opportunity to expand the single-channel adapter to a two-channel design. This then permits a mixture of two streams that is nearly free of dead volume and that can be added using two pipettes or other connectors.

EMBODIMENT(S)

Chromatography

The adapter permits the activation of miniature chromatography columns in order to operate them under flow-through. This permits parallelization of chromatography experiments that can be performed analogous to all current techniques on the laboratory scale on pipetting platforms (HTS applications). Using this technique it is possible to attain better results in the purification of molecules on the micro-measure scale since the separating potential of columns can be utilized. Moreover, this technique permits parallel use of columns for developing chromatography processes. The technique furthermore permits different chromatography materials to be tested for their quality for different applications.

Membrane Chromatography:

Another example is found in the continuous activation of membranes or membrane stacks. The breadth of application is similar to that described in the foregoing. The technique furthermore permits very different membrane materials to be tested for their quality for different applications.

Filtration:

Filter plates can be loaded continuously using this method and thus large quantities of material to be filtered can be applied. This is suitable for generating both a large quantity of filtrate and also retentate (e.g. cells, inclusion bodies). The technique furthermore permits testing of different filter materials for their quality for different applications.

The invention claimed is:

1. An adapter in combination with a vessel, the adapter comprising:
    an input having an upper bore for receiving an essentially needle-shaped structure for metering samples, the upper bore in communication with a lower bore, the lower bore opening into an output;
    a first seal for surrounding in a liquid-tight manner the essentially needle-shaped structure upon entering the adapter;
    a second seal spaced from the first seal enabling a liquid-tight connection of the output to the vessel, the vessel having a column-like shape and being filled with a stationary porous solid mass;
    whereby the adapter enables the essentially needle-shaped structure to be received in a liquid-tight manner and seals in a liquid-tight manner with the vessel upon which the adapter is placed;
    wherein the vessel defines a bore having a countersink upper portion and a reduced diameter lower portion, the second seal surrounding a reduced diameter portion of the adapter and seated within the countersink portion, the reduced diameter portion of the adapter extending into the reduced diameter lower portion of the bore.

2. The adapter in combination with a vessel in accordance with claim 1, wherein the input is funnel-shaped.

3. The adapter in combination with a vessel in accordance with claim 1, wherein the input is provided with the first seal.

4. The adapter in combination with a vessel in accordance with claim 1, wherein the first seal is an O-ring.

5. The adapter in combination with a vessel in accordance with claim 1, wherein the lower bore receives a tip of the essentially needle-shaped structure.

6. The adapter in combination with a vessel in accordance with claim 1, wherein the output is equipped with means that enable uniform exit of a liquid volume across the entire cross-section.

7. The adapter in combination with a vessel in accordance with claim 6, wherein the output is equipped with a membrane, perforated plate, or filter disk.

8. The adapter in combination with a vessel in accordance with claim 1, wherein a lower area of the adapter that can be inserted into the vessel is dimensioned such that it forms with the bottom of the vessel largely no empty space.

9. The adapter in combination with a vessel in accordance with claim 1, wherein the second seal is arranged in a side of the adapter facing the vessel.

10. The adapter in combination with a vessel in accordance with claim 1, wherein the adapter has at least two inputs that are combined to create a manifold passage that enters into a bore.

11. The adapter in combination with a vessel in accordance with claim 1, wherein the adapter is embodied in two parts with an upper part and a lower part.

12. The adapter in combination with a vessel in accordance with claim 11, wherein the upper part and the lower part are connected to one another in a liquid-tight manner.

13. An adapter system in combination with a vessel in accordance with claim 1, wherein at least a second adapter is arranged together with the first adapter.

14. The adapter system in accordance with claim 13, wherein the at least two adapters are connected to one another.

15. The adapter system in accordance with claim 13, wherein a plurality of adapters are arranged in geometrical arrangements.

16. The adapter system in accordance with claim 15, wherein the arrangement is a rectangular grid, a circle or circle segment, an arc, or a row.

17. The adapter system in accordance with claim 15, wherein the arrangement includes 2, 4, 8, or 96 adapters.

18. The adapter in combination with a vessel in accordance with claim 1, wherein the adapter is permanently connected to the vessel.

19. The adapter in combination with a vessel in accordance with claim 1, wherein the input is provided with seal means that make it possible to add a sample in a liquid-tight manner.

20. The adapter in combination with a vessel in accordance with claim 19, wherein the input is equipped with a liquid-tight connection that makes it possible to attach a tube-like sample feed line.

21. A method for adding samples or purifying substances in which at least one of a sample and a purifying substance is added to a vessel having a column-like shape, the vessel being filled with a stationary porous solid mass, wherein an adapter is placed onto the vessel, the adapter in combination with the vessel being in accordance with claim 1.

22. The method in accordance with claim 21, wherein the adapter is fed the sample in continuous operation.

23. The method in accordance with claim 21, wherein the vessel is used with a filter, absorber, or membrane.

24. The method in accordance with claim 21, wherein at least two different liquids are mixed with one another that are added to different inputs of the adapter and pass through a manifold passage before they are fed to the vessel.

25. The method in accordance with claim 21, wherein at least two vessels are activated at the same time.

26. The adapter in combination with a vessel in accordance with claim 1, in further combination with the essentially needle-shaped structure.

27. The adapter in combination with a vessel in accordance with claim 1, wherein the solid mass within the vessel is one of a filter, a membrane, a liquid-distributing substrate and a chromatography substance.

28. The adapter in combination with a vessel in accordance with claim 1, wherein the vessel is at least one of a small column and a miniature chromatography column.

29. The adapter in combination with a vessel in accordance with claim 1, wherein the first seal is arranged in a region between the upper and the lower bore.

30. The adapter in combination with a vessel in accordance with claim 1, wherein the second seal circumferentially surrounds a reduced diameter portion of the adapter and is in contact with both the adapter and a countersink portion of the vessel.

31. An adapter in combination with a vessel, the adapter comprising:
    an input having an upper bore for receiving an essentially needle-shaped structure for metering samples, the upper bore in communication with a lower bore, the lower bore opening into an output;

a first seal for surrounding in a liquid-tight manner the essentially needle-shaped structure upon entering the adapter;

a second seal spaced from the first seal enabling a liquid-tight connection of the output to the vessel, the vessel having a column-like shape and being filled with a stationary porous solid mass;

wherein the lower bore receives a tip of the essentially needle-shaped structure;

whereby the adapter enables the essentially needle-shaped structure to be received in a liquid-tight manner and seals in a liquid-tight manner with the vessel upon which the adapter is placed;

wherein the vessel defines a bore having a countersink upper portion and a reduced diameter lower portion, the second seal surrounding a reduced diameter portion of the adapter and seated within the countersink portion, the reduced diameter portion of the adapter extending into the reduced diameter lower portion of the bore.

32. The adapter in combination with a vessel in accordance with claim 31, wherein the second seal is in contact with both the adapter and a countersink portion of the vessel.

33. An adapter in combination with a vessel, the adapter comprising:

an input having an upper bore for receiving an essentially needle-shaped structure for metering samples, the upper bore in communication with a lower bore, the lower bore opening into an output;

a first seal for surrounding in a liquid-tight manner the essentially needle-shaped structure upon entering the adapter;

a second seal spaced from the first seal enabling a liquid-tight connection of the output to the vessel having a column-like shape and being filled with a stationary porous solid mass;

wherein the second seal is arranged in a side of the adapter facing the vessel;

whereby the adapter enables the essentially needle-shaped structure to be received in a liquid-tight manner and seals in a liquid-tight manner with the vessel upon which the adapter is placed;

wherein the vessel defines a bore having a countersink upper portion and a reduced diameter lower portion, the second seal surrounding a reduced diameter portion of the adapter and seated within the countersink portion, the reduced diameter portion of the adapter extending into the reduced diameter lower portion of the bore.

34. The adapter in combination with a vessel in accordance with claim 33, in combination with the essentially needle-shaped structure.

35. The adapter in combination with a vessel in accordance with claim 34, wherein the second seal circumferentially surrounds a reduced diameter portion of the adapter and is in contact with both the adapter and a countersink portion of the vessel.

\* \* \* \* \*